(12) United States Patent
Sigmon, Jr. et al.

(10) Patent No.: US 11,452,798 B2
(45) Date of Patent: *Sep. 27, 2022

(54) CROSSLINKING SUBMUCOSAL INJECTATE SYSTEM

(71) Applicant: Cook Medical Technologies LLC, Bloomington, IN (US)

(72) Inventors: John C. Sigmon, Jr., Winston-Salem, NC (US); Shaun D. Gittard, Winston-Salem, NC (US); Gregory J. Hardy, Colonie, NY (US); Christopher A. Carruthers, Winston-Salem, NC (US); Darin G. Schaeffer, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,005

(22) Filed: Sep. 27, 2018

(65) Prior Publication Data

US 2019/0091374 A1    Mar. 28, 2019

Related U.S. Application Data

(60) Provisional application No. 62/563,912, filed on Sep. 27, 2017.

(51) Int. Cl.
| | |
|---|---|
| *A61L 27/52* | (2006.01) |
| *A61L 27/38* | (2006.01) |
| *A61L 27/22* | (2006.01) |
| *A61L 27/36* | (2006.01) |
| *A61L 27/24* | (2006.01) |
| *A61L 27/20* | (2006.01) |
| *A61L 31/14* | (2006.01) |
| *A61L 31/04* | (2006.01) |

(52) U.S. Cl.
CPC .............. *A61L 27/52* (2013.01); *A61L 27/20* (2013.01); *A61L 27/222* (2013.01); *A61L 27/227* (2013.01); *A61L 27/24* (2013.01); *A61L 27/3687* (2013.01); *A61L 27/3882* (2013.01); *A61L 31/042* (2013.01); *A61L 31/14* (2013.01)

(58) Field of Classification Search
CPC combination set(s) only.
See application file for complete search history.

(56) References Cited

U.S. PATENT DOCUMENTS

| | | | |
|---|---|---|---|
| 4,241,176 A | 12/1980 | Avrameas et al. |
| 4,517,173 A | 5/1985 | Kizawa et al. |
| 4,650,472 A | 3/1987 | Bates |
| 4,710,172 A | 12/1987 | Jacklich et al. |
| 4,740,203 A | 4/1988 | Hoskins et al. |
| 5,240,626 A | 8/1993 | Thakur et al. |
| 5,260,066 A | 11/1993 | Wood et al. |
| 5,542,948 A | 8/1996 | Weaver et al. |
| 5,702,630 A | 12/1997 | Sasaki et al. |
| 6,251,063 B1 | 6/2001 | Silverman |
| 6,348,502 B1 | 2/2002 | Gardiner et al. |
| 6,395,307 B1 | 5/2002 | Banning et al. |
| 6,599,496 B2 | 7/2003 | Carter et al. |
| 6,607,512 B2 | 8/2003 | Oliver et al. |
| 6,916,308 B2 | 7/2005 | Dixon et al. |
| 7,131,997 B2 | 11/2006 | Bourne et al. |
| 7,303,759 B2 | 12/2007 | Mershon |
| 7,332,160 B2 | 2/2008 | Freyman et al. |
| 7,611,542 B2 | 11/2009 | Bourne et al. |
| 7,906,508 B2 | 3/2011 | Koga et al. |
| 8,827,980 B2 | 9/2014 | Ji |
| 9,867,931 B2 | 1/2018 | Gittard |
| 2002/0168334 A1 | 11/2002 | Jacob et al. |
| 2003/0225460 A1 | 12/2003 | Gostout et al. |
| 2004/0101564 A1 | 5/2004 | Rioux et al. |
| 2004/0225247 A1 | 11/2004 | Pugsley et al. |
| 2005/0181023 A1 | 8/2005 | Young et al. |
| 2005/0281775 A1 | 12/2005 | Carrington et al. |

(Continued)

FOREIGN PATENT DOCUMENTS

| | | |
|---|---|---|
| CN | 102006893 A | 4/2011 |
| EP | 1 352 661 A1 | 10/2003 |

(Continued)

OTHER PUBLICATIONS

Giday; "Preliminary Data on the Nanopowder Hemostatic Agent TC-325 to Control Gastrointestinal Bleeding"; Gastroenterology & Hepatology, vol. 7, Issue 9; Sep. 2011; pp. 620-622.

Patel et al., "Formulation and evaluation of stomach-specific amoxicillin-loaded carbopol-934P mucoadhesive microspheres for ant\-Helicobacter pylori therapy," *Journal of Microencapsulation*, 26(4); Jun. 1, 2009; pp. 365-376.

Potts, et al., "Oesophageal bandaging: a new opportunity for thermosetting polymers," *STP Pharm S*, 10(4); Jul. 1, 2000; pp. 293-301.

Richardson, et al., "The Bioadhesive and Swelling Characteristics of Sodium Alginate Suspensions," http://pubs.rsc.org, Oct. 21, 2009; 9 pages.

(Continued)

*Primary Examiner* — Hasan S Ahmed
(74) *Attorney, Agent, or Firm* — Crowell & Moring LLP (57) ABSTRACT

A method of treating a lesion in a gastrointestinal tract and an injectate system are provided. The method includes injecting a crosslinkable gel into a first tissue layer, the crosslinkable gel increasing a volume of the first tissue layer. The method also includes providing a crosslinker and resecting a portion of a first tissue layer having the increased volume away from a second tissue layer creating an exposed region in a remaining portion of the first layer and leaving a portion of the gel covering at least a portion of the exposed region. The injectate system includes a crosslinkable gel and a crosslinker where the crosslinkable gel and the crosslinker form a crosslinked gel having a compressive modulus of about 10-500 kPa.

17 Claims, 7 Drawing Sheets

(56) References Cited

U.S. PATENT DOCUMENTS

| | | |
|---|---|---|
| 2007/0179590 A1 | 8/2007 | Lu et al. |
| 2007/0207192 A1 | 9/2007 | Holl et al. |
| 2007/0281007 A1 | 12/2007 | Jacob et al. |
| 2007/0287958 A1 | 12/2007 | McKenzie et al. |
| 2008/0060970 A1 | 3/2008 | Wheeler et al. |
| 2008/0108860 A1 | 5/2008 | Bell et al. |
| 2008/0287907 A1 | 11/2008 | Gregory et al. |
| 2009/0010997 A1 | 1/2009 | Haley |
| 2009/0125031 A1 | 5/2009 | Melsheimer et al. |
| 2009/0169471 A1 | 7/2009 | Richard et al. |
| 2009/0181074 A1 | 7/2009 | Makower |
| 2009/0181079 A1 | 7/2009 | Zhao et al. |
| 2009/0281549 A1 | 11/2009 | Dixon |
| 2010/0016808 A1 | 1/2010 | Groppi |
| 2010/0129427 A1 | 5/2010 | Hen et al. |
| 2010/0216754 A1 | 8/2010 | Hill |
| 2011/0097376 A1 | 4/2011 | Berlemann et al. |
| 2011/0097401 A1 | 4/2011 | Phillips et al. |
| 2011/0189259 A1 | 8/2011 | Vasisht et al. |
| 2011/0208158 A1 | 8/2011 | Sigmon, Jr. et al. |
| 2011/0301525 A1* | 12/2011 | Nicoll ................. A61L 27/20 604/20 |
| 2011/0305768 A1 | 12/2011 | Mao et al. |
| 2012/0237566 A1 | 9/2012 | Ray et al. |
| 2013/0231753 A1 | 9/2013 | Liddy et al. |
| 2014/0271491 A1 | 9/2014 | Gittard et al. |

FOREIGN PATENT DOCUMENTS

| | | |
|---|---|---|
| GB | 2435425 A | 8/2007 |
| JP | H 11501652 A | 2/1999 |
| JP | 2002-338456 A | 11/2002 |
| JP | 2003-153911 A | 5/2003 |
| JP | 2003 225 242 A | 8/2003 |
| JP | 2004-313369 A | 11/2004 |
| JP | 2007-75569 A | 3/2007 |
| JP | 2009 254 874 A | 11/2009 |
| JP | 2011-507665 A | 3/2011 |
| JP | 2016-506949 A | 3/2016 |
| WO | WO 1996/21432 A1 | 7/1996 |
| WO | WO 1996/2591 A | 8/1996 |
| WO | WO 2000/12018 A1 | 3/2000 |
| WO | WO 2002/064113 A1 | 8/2002 |
| WO | WO 2005/069831 A2 | 8/2005 |
| WO | WO 2005/097239 A1 | 10/2005 |
| WO | WO 2007/074327 A1 | 7/2007 |
| WO | WO 2008/051561 A2 | 5/2008 |
| WO | WO 2009/088726 A2 | 7/2009 |
| WO | WO 2010/056899 A1 | 5/2010 |
| WO | WO 2014/119836 A1 | 8/2014 |
| WO | WO 2014/149617 A1 | 9/2014 |

OTHER PUBLICATIONS

Richardson, et al., "Oesophageal bioadhesion of sodium alginate suspensions 2. Suspension behavior on oesophageal mucosa," *Eur J Pharm Sci.*, 24(1); Jan. 1, 2005; pp. 107-114.

Richardson, et al., "Oesophageal bioadhesion of sodium alginate suspensions particle swelling and mucosal retention," *Eur. J. Pharm Sci.*, 23(1); Sep. 1, 2004; pp. 49-56.

Tang, et al., "Bioadhesive oesophageal bandages: protection against acid and pepsin injury," *Int J. Pharm*, 292(1-2); Mar. 23, 2005; pp. 169-177.

Yamasaki, MD et al.; "A novel method of endoscopic submucosal dissection with blunt abrasion by submucosal injection of sodium carboxymethylcelulose: an animal preliminary study"; Gastrointestinal Endoscopy; vol. 64, No. 6; Dec. 1, 2006; pp. 958-965.

International Search Report dated Dec. 21, 2018 for International Application No. PCT/US2018/053060.

Written Opinion dated Dec. 21, 2018 for International Application No. PCT/US2018/053060.

\* cited by examiner

CROSSLINKING SUBMUCOSAL INJECTATE SYSTEM

RELATED APPLICATIONS

This application claims the benefit of U.S. Provisional Application No. 62/563,912, filed Sep. 27, 2017, which is incorporated by reference herein in its entirety.

BACKGROUND

1. Technical Field

The present invention relates to devices and methods for treating lesions in the gastrointestinal tract, such as lesions arising from the disorders of the gastrointestinal tract and/or medical procedures that require bulking of the gastrointestinal tract or removal of the mucosal and a portion of the submucosal layers of gastrointestinal tract wall and protection of the exposed tissue after removal of the lesion. In particular, the present invention relates to a crosslinking submucosal injectate system and method.

2. Background Information

There are several disorders of the gastrointestinal tract, e.g., gastrointestinal inflammation, gastrointestinal cancer, gastrointestinal infection, gastrointestinal motility dysfunction, or lesions, wounds or contusions of tissue of a portion of the gastrointestinal tract that can cause gastrointestinal lesions. In addition, there are a wide variety of medical procedures that require removal of the mucosal or submucosal layers of gastrointestinal tract wall and can also cause injury or lesions in the gastrointestinal tract. There are also medical procedures that require separating tissues, such as removal of oral lymphoid tissue away from underlying tissue in the mouth and neck. Non-limiting examples include tonsillectomies, adenoidectomies, oral tumor resections or other iatrogenic oral lesions. Other procedures include endoscopic mucosal resection (EMR), endoscopic submucosal dissection (ESD), polypectomy, per-oral endoscopic myotomy, biopsy, and ablation (thermal, chemical, radiofrequency, and cryogenic). As with the disorders of the gastrointestinal tract, similar adverse events can occur after removal of the mucosal or submucosal layers, including bleeding and stricturing.

Figure 1:
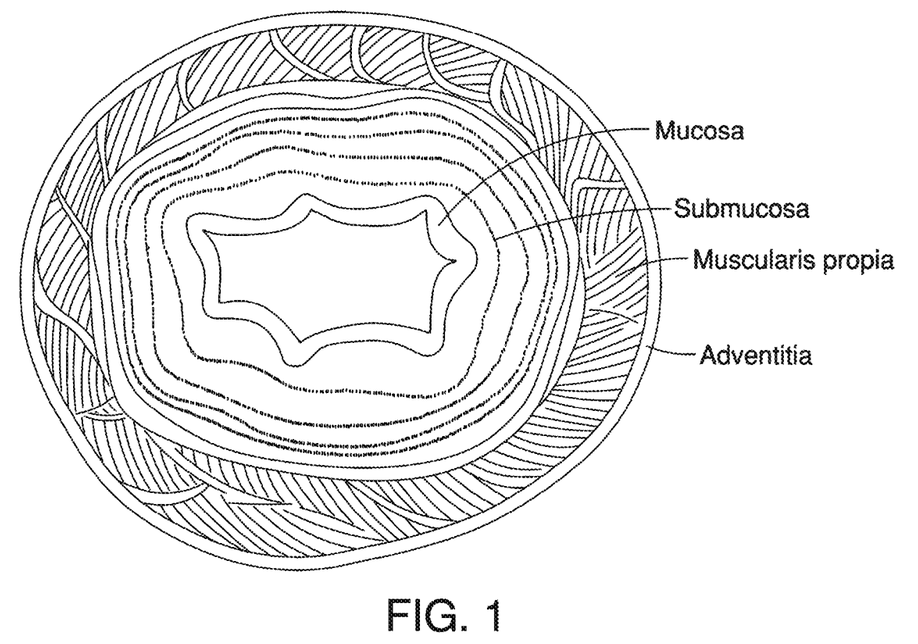
FIG. 1 is an illustration of the layers of the gastrointestinal tract.

Safe removal of a lesion from the gastrointestinal track can be challenging. The walls of the gastrointestinal tract include multiple tissue layers as shown in FIG. 1. Removal of one or more layers, for example the mucosa or the mucosa and submucosa, without damaging the underlying layers that remain after removal of the outer layer is difficult. Bleeding and perforation of the underlying layer may occur. In addition, after the removal of one or more layers, the underlying tissue is exposed to the contents of the gastrointestinal tract. With the protective layer of the mucosa removed, the underlying tissue can be damaged. For example, stomach acid or digestive enzymes may harm the underlying tissue which can lead to post resection complications such as delayed bleeding, ulcer formation, scar formation and stricturing. With respect to removal of oral lymphoid tissue, challenges also exist. Antibiotics do not help reduce post-surgery pain or healing with tonsillectomies or adenoidectomies. Antibiotics are not prescribed unless an infection arises later.

New and improved systems and methods for separation of the tissue layers that minimize the risk of bleeding and perforation and systems and methods for protective coverings over the newly exposed tissues are highly desirable. Systems and methods that will protect the healing wound from the harmful bacteria and food that impedes the healing process and causes inflammation when oral lymphoid tissue is removed are also desirable. These systems and methods can reduce pain and decrease healing time. The systems and methods described herein will also help reduce pain by protecting exposed nerve endings from being triggered from things like eating, swallowing, talking, breathing by providing a protective covering.

SUMMARY

In one embodiment, a method of treating a lesion in a gastrointestinal tract is provided. The method includes injecting a crosslinkable gel into a first tissue layer where the crosslinkable gel increases a volume of the first tissue layer. The method also includes providing a crosslinker and resecting a portion of the first tissue layer having the increased volume away from a second tissue layer creating an exposed region in a remaining portion of the first layer and leaving a portion of the gel covering at least a portion of the exposed region of the first tissue layer.

In one embodiment, an injectate system is provided. The injectate system includes a crosslinkable gel and a crosslinker for crosslinking the gel, so that the crosslinkable gel and the crosslinker form a crosslinked gel having a compressive modulus of about 10-500 kPa.

In one embodiment, method of increasing a thickness of a tissue layer is provided. The method includes injecting a crosslinkable gel into a tissue layer to increase the thickness of the tissue layer, providing a crosslinker to the tissue layer and crosslinking the crosslinkable gel.

DETAILED DESCRIPTION

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the injectable solution to a patient. Hence the term "distal" means the portion of the device that is farthest from the physician and the term "proximal" means the portion of the device that is nearest to the physician.

The present invention relates to methods and devices to facilitate resection of mucosal and a portion of submucosal tissue and methods for protecting or treating lesions in the gastrointestinal tract resulting from disorders of the gastrointestinal tract and/or medical procedures that require removal of one or more layers of the gastrointestinal tract, such as the mucosal and submucosal layers of gastrointestinal tract or oral lymphoid tissue and methods for increasing the thickness of a tissue layer. By way of non-limiting example, the procedures performed in the gastrointestinal tract may include endoscopic submucosal dissection, endoscopic mucosal resection, polypectomy, tonsillectomy, adenoidectomy, oral tumor resection, and combinations thereof. Examples of disorders include ulcer, cancer, varices, Barrett's esophagus, iatrogenic oral lesions or a combination thereof. The present invention relates to a submucosal injectate that both facilitates safe removal of mucosal and a portion of submucosal tissue or oral lymphoid tissue and additionally provides a protective coating to the newly exposed underlying tissue layers. In some embodiments, the crosslinkable gel and the crosslinker may be used to increase the thickness of a tissue layer. Non-limiting examples of disorders that may be treated by modifying the thickness of a tissue include injections of the injectate solution into the submucosa to treat Gastro-esophageal reflux disease (GERD) or fecal incontinence.

The protective coating is provided to protect or treat the site from further injury or infection, slow or stop bleeding, prevent delayed bleeding, prevent delayed perforation, seal anastomotic leaks or fistulas, and/or promote healing at the exposed site. The protective covering remains at and about the lesion site for a time sufficient to allow the site to be treated or healed (minimum of 30 minutes; preferably 24 hours; more preferably at least 48 or 72 hours; most preferably the protective covering is capable of remaining at and about the lesion site for 24-72 hours or longer; hence the term "long-lasting" refers to the time period that a protective covering of the present invention remains at and about the lesion and means anywhere from 30 minutes to 72 hours or longer). The term "protect" refers to protecting the site of the lesion from further injury or infection. The term "treat" refers to slowing or stopping bleeding at the site of the lesion, preventing delayed bleeding, preventing delayed perforation of the lesion, and/or promoting healing at the exposed site of the lesion, and/or promoting new tissue formation. The term "heal" in reference to a lesion refers to a process of repairing the gastrointestinal tissue by natural processes, as by, for example, scar formation so that following "healing" the lesion is at least reduced in size as compared to the initial size of the lesion or absent.

Figure 2:
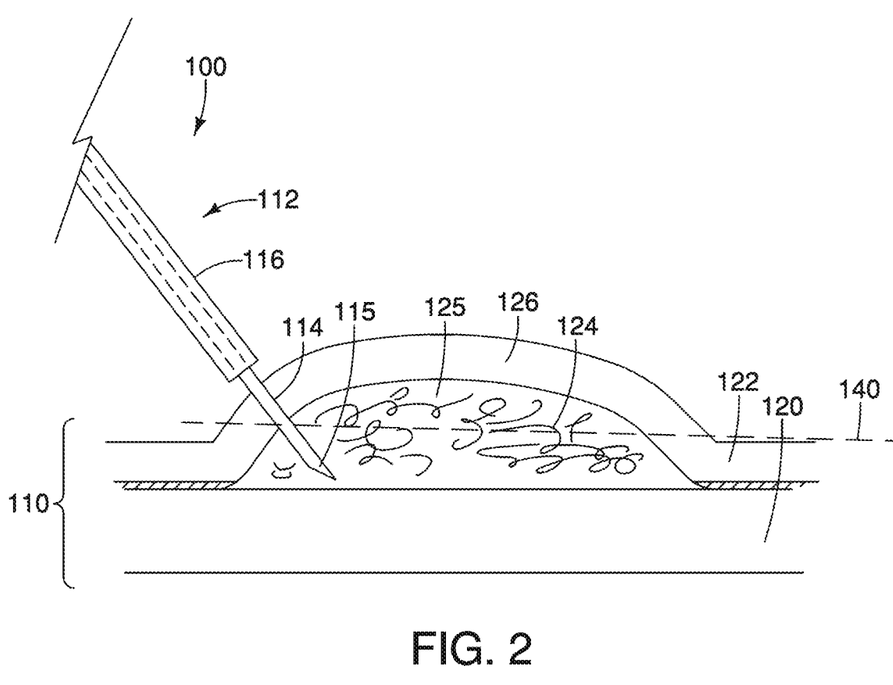
FIG. 2 is a sectional view of an injectate solution of an embodiment described herein being delivered using a delivery system.

FIG. 2 illustrates a delivery device 100 for delivering an injectate solution to a tissue treatment site 110. A distal portion 112 of the delivery device 100 is shown in FIG. 2. The delivery device 100 may include a catheter 114 having a sharpened tip 115, such as a needle, to facilitate entry of the catheter 114 into the submucosal space. In some embodiments, the catheter 114 may include an outer catheter 116 that coextends with the catheter 114 and can cover the sharpened tip 115 for delivery to the treatment site 110. At the site, the catheter 14 may be extended from the outer catheter 116 for insertion of the tip 115 into the tissue 110. As shown in FIG. 2, the catheter 114 may inserted into a first layer of tissue 120 to add volume to the first layer of tissue 120. As shown in FIG. 2, the injection of an injectate solution 124 into the first layer 120 raises the first layer and one or more adjacent layers 122 to bulk the tissue or facilitate resection a portion of the second layer 122 from the first layer 120 by creating an elevated portion 126. The layers 120, 122 may be any adjacent layers of tissue, for example, the muscularis and submucosal layers. In some embodiments, the injectate solution 124 may be injected into the submucosa to facilitate resection of a portion of the submucosal layer away from the muscularis layer without perforating the muscularis layer. The mucosal layer may be removed together with the portion of the resected submucosal layer. In some embodiments, the injectate solution 124 may break the attachments between the tissue layers 120, 122. The elevated tissue portion 126 may then be resected by the physician using an electrocautery device or snare. In some embodiments, a portion of the submucosal layer is removed and a portion of the submucosal layer remains connected to the muscularis layer so that the muscularis layer is not perforated during the removal procedure. One skilled in the art will understand how much of the submucosal layer to remove during the procedure while leaving the muscularis layer intact.

Figure 3:
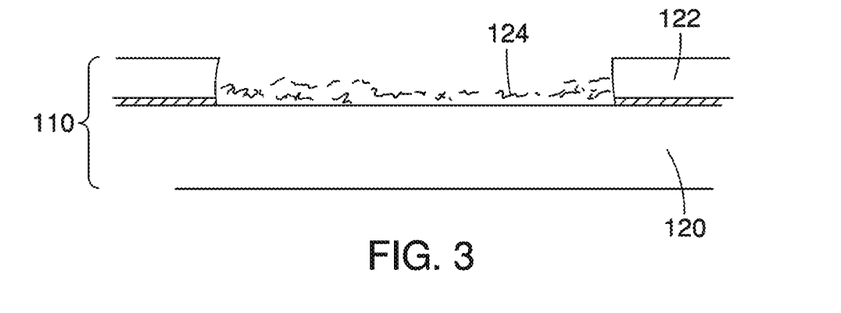
FIG. 3 is a sectional view of the injectate solution at the site after removal of a layer of tissue.

FIG. 3 illustrates the treatment site 110 after the elevated tissue portion 126 shown in FIG. 2 has been removed. FIG. 3 illustrates that a portion of the injectate solution 124 may remain at the site 110 after the elevated tissue portion 126 has been removed. The injectate solution 124 may be entangled with fibers from the portion of the second layer remaining with the first layer. The remainder of the injectate solution 124 and the remainder of the second layer 122 have been removed. The injectate solution 124 may be crosslinked before or after the elevated tissue portion 126 is removed as explained in more detail below. Where the injectate solution 124 is used to bulk the tissue, the injectate solution 124 may be injected into a layer of tissue to increase the volume of the tissue without any further procedure.

Figures 10, 11A, 11B:
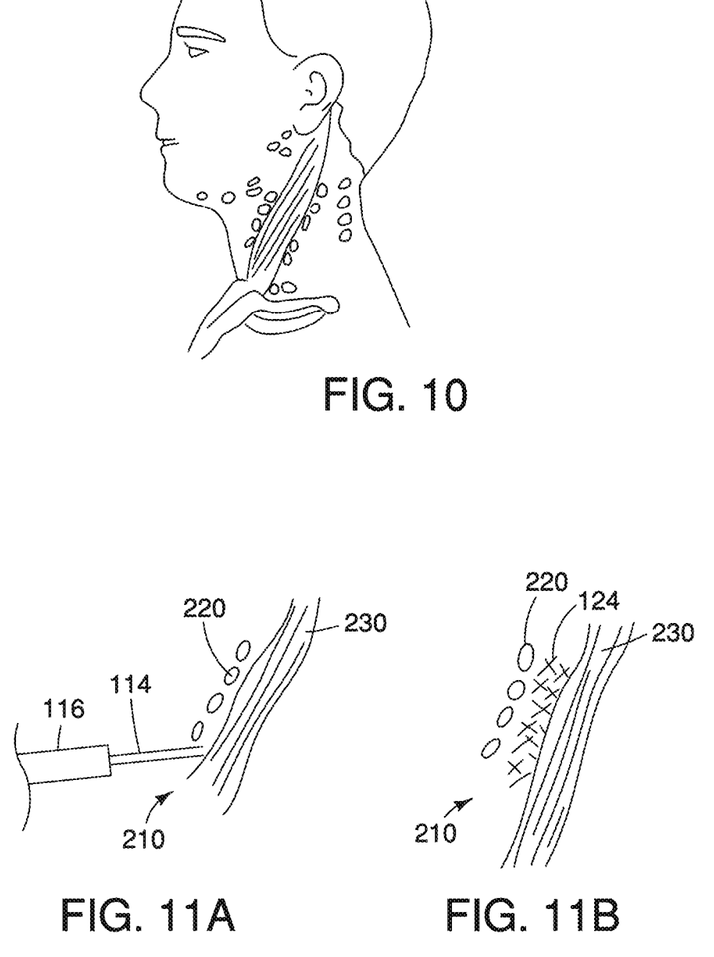
FIG. 10 illustrates oral lymphoid tissue in the head and neck.
FIGS. 11A-11C illustrate an embodiment showing the crosslinked injectate solution being employed to remove oral lymphoid tissue from underlying muscle tissue.

In some embodiments, the injectate solution 124 may be used to separate oral lymphoid tissue from tissue, such as muscle. Oral lymphoid tissue includes lymph nodes, adenoids and tonsils. FIG. 10 illustrates oral lymphoid tissue in the head and neck that may be removed using the injectate solution. As shown in FIG. 11A, the catheter 114 may inserted at a treatment site 210 between oral lymphoid tissue 220 and muscle tissue 230. As shown in FIG. 11B, the injection of an injectate solution 124 between the oral lymphoid tissue 220 raises the oral lymphoid tissue 220 away from the muscle tissue 230 to facilitate resection the oral lymphoid tissue 220. In some embodiments, the injectate solution 124 may break the attachments between the oral lymphoid tissue 220 and the muscle tissue 230. The oral lymphoid tissue 220 may then be resected by the physician using an electrocautery device or snare. A portion of the injectate solution 124 may be removed with the oral lymphoid tissue 220.

Figure 11C:
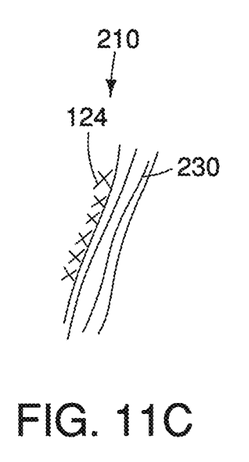

FIG. 11C illustrates the treatment site 210 after the oral lymphoid tissue 220 have been removed. FIG. 11C illustrates that a portion of the injectate solution 124 may remain at the site 210 after the oral lymphoid tissue 220 been removed. The injectate solution 124 may be entangled with fibers from the muscle tissue 230. The remainder of the injectate solution 124 and oral lymphoid tissue 220 have been removed. The injectate solution 124 may be crosslinked before or after the oral lymphoid tissue portion is removed as explained in more detail below.

In some embodiments, the injectate solution 124 may include a gel, such as a crosslinkable hydrogel, but are not limited thereto. Hydrogels as used herein are crosslinkable hydrophilic polymer structures that can imbibe large amounts of water or biological fluids. Examples of suitable crosslinkable gels include, but are not limited to the following including agarose, alginate, Carbomer, carboxymethyl cellulose, collagen, fibronectin, chitosan, chondroitin sulfate, dextran, polyethylene glycol, polyvinylpyrolidone, silicone, poly (hydroxyethyl methacrylate), polyacrylic acid, polyacrylamide, polyvinyl alcohol, gelatin, mucin, heparin, hyaluronan and combinations thereof. In some embodiments, crosslinking of the injectate solution 124 may occur via electrostatic or covalent crossing linking. Examples of electrostatic cross linkers include but are not limited to ligand-receptor interactions (e.g. streptavidin-biotin interactions) or ionic interactions from molecules containing divalent and trivalent elements magnesium chloride ($MgCl_2$), calcium chloride ($CaCl_2$), strontium chloride ($SrCl_2$), barium chloride ($BaCl_2$), aluminum sulfate $Al_2(SO_4)_3$, barium sulfate ($BaSO_4$), calcium carbonate ($CaCo_3$), ferric chloride ($FeCl_3$) and ferrous chloride ($FeCl_2$). Covalent crosslinking may be achieved by inclusion of a free radical generator, click chemistry, Schiff base reactions, and enzyme-mediated reactions. In some embodiments, stimuli-responsive injectate solutions 124 may be used that include components(s) that trigger the crosslinking process. Non-limiting examples of stimuli include light activation (added photo initiator), temperature activation or pH activation (added acid or base).

In some embodiments, the injectate solution 124 may be delivered to the site as a single injection where the components of the injectate solution including the gel and the crosslinker are mixed in the delivery system or combined at the treatment site to initiate the crosslinking in the single injection. In some embodiments, the injectate solution may be delivered as separate components of a multicomponent system where the crosslinkable gel is delivered to the treatment site separate from the crosslinker. For embodiments having separate delivery, the crosslinkable gel may be delivered first followed by the crosslinker or the crosslinker may be delivered first followed by the crosslinkable gel. Combinations of single injection and multiple component delivery systems may be used together depending on the treatment and the size of the area to be covered by the injectate solution. In some embodiments, the saline may be delivered to the treatment site before, during or after the injectate solution is delivered. In some embodiments, a catheter may be used to deliver the injectate solution in a sequential delivery where the crosslinkable gel is delivered to the site first. The catheter may be rinsed with saline prior to delivery of the crosslinker through the same catheter. In some embodiments, the crosslinker may be first delivered to the treatment site using a catheter, followed by a saline rinse of the catheter and subsequent crosslinkable gel delivery through the same catheter.

In some embodiments, the injectate solution may be injected into the submucosa and penetrate in the submucosal space between the submucosal fibers, which results in an elevated portion of the submucosal and mucosal layers away from the muscularis layer. The tissue elevation from the injectate solution facilitates safe resection of the submucosal fibers or the oral lymphoid tissue since the injectate solution is located above and below the resection plane. (See FIG. 2 showing an example of a resection plane 140.) The injectate solution above the resection plane (intraluminal side) is removed with the resected tissue. The injectate solution below the resection plane remains imbedded in the remaining submucosal fibers. The tissue may be resected with a crosslinked injectate solution or an uncrosslinked injectate solution. With the uncrosslinked injectate resection, the gel is viscous enough to penetrate into the submucosal space between the submucosal fibers. The tissue may be resected using the uncrosslinked injectate solution to lift the tissue and the crosslinking of the gel may be completed after the tissue has been resected and a portion of the uncrosslinked injectate solution remains over the inner layer of tissue. In some embodiments, a liquid crosslinker may be flushed over the treatment site and the remaining gel at the treatment site. In embodiments where the crosslinking is initiated after resection of the tissue, the application of the crosslinker may be more tightly controlled. For example, the crosslinker or the crosslinking mechanism (e.g. light initiation) may be applied only to the exposed gel at the treatment site to minimize or eliminate collateral damage from the crosslinking agent. In some embodiments, the cross linking agent is more toxic than the crosslinkable gel. When the crosslinking is initiated after resection of the tissue, the crosslinker may be injected but does not need to be injected, but instead may be dripped, sprayed or exposed (via light) to the crosslinkable gel at the treatment site.

Regardless of the delivery used for the injectate solution, the viscosity of the injectate solution should be viscous enough to penetrate into the submucosal fibers and still be fluid enough to deliver through a catheter or other delivery system into the gastrointestinal tract. In addition, the viscosity of the injectate solution should also have the appropriate viscosity to penetrate into the submucosa and not leak around the injection site because the injectate solution is too viscous to enter into the injection site. In some embodiments, the maximum viscosity of the injectate solution should be about 120,000 cP, preferably the maximum viscosity of the injectate solution should be about 100,000 cP.

In some embodiments, the pressure at which the injectate solution is injected into the treatment site is provided within a range of pressure that allows for the injectate solution to penetrate into the submucosal fibers but does not penetrate into the muscularis layer. In some embodiments, the pressure range for delivering the injectate solution to the treatment site may be about 0.25 psi to about 5 psi.

The injectate solution may be crosslinked so that the final crosslinked gel has a compressive modulus in a specified range. In some embodiments, the crosslinked gel may have a compressive modulus of about 10-500 kPa, preferably in the range of about 100-500 kPa.

In some embodiments, the time range for the crosslinking may be controlled. For example, when the gel and the crosslinker are delivered in a single injection or when the injectate solution is crosslinked before the resection, the injectate solution should remain flowable to the treatment site so that the injectate flows into the submucosal fibers but the physician does not need to wait too long before preforming the resection. In some embodiments, the crosslinked injectate solution should reach an acceptable compressive modulus between about 0.5 seconds to about 30 minutes. An example of a gel and a crosslinker that when combined would not meet the time range of about 0.5 seconds to about 30 minutes is alginate with $CaCO_3$. $CaCo_3$ is poorly soluble in water which results in slow release of calcium so that the time exceeds 30 minutes with the combination of alginate before the acceptable compressive modulus is achieved. Examples of suitable combinations for the injectate solution are shown in Table 1, but are not limited thereto.

TABLE 1

Injectate Solutions

| Gel | Crosslinker |
| --- | --- |
| Carboxymethyl cellulose | $Al_3(SO_4)_3$ |
| Carboxymethyl cellulose | $Fe(III)Cl_3$ |
| Carboxymethyl cellulose | $CaCl_2$ |
| Carboxymethyl cellulose | $SrCl_2$ |
| Carboxymethyl cellulose | $MgCl_2$ |
| Carboxymethyl cellulose | $CaCo_3$ with gluconic acid |
| Alginate | $SrCl_2$ |

The crosslinked injectate solution remains at and about the treatment site for a time sufficient to allow the site to be treated or healed. In some embodiments, the crosslinked injectate solution remains at the treatment site for at least about 24 hours, preferably about 72 hours or longer.

Figure 4:
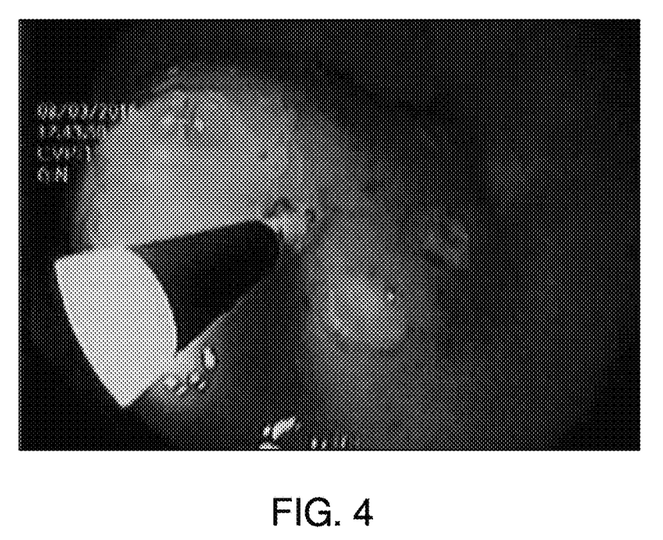
FIG. 4 illustrates an embodiment showing a raised mucosal and submucosal tissue that occurs after the injectate solution has been injected into the submucosa.
Figure 5A:
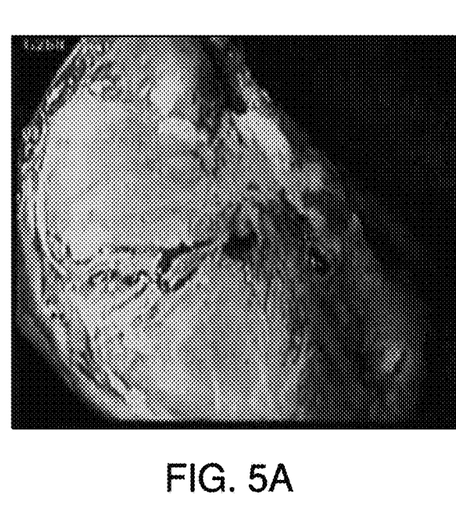
FIG. 5A illustrates the lesion after the mucosa and submucosa have been resected.
Figure 5B:
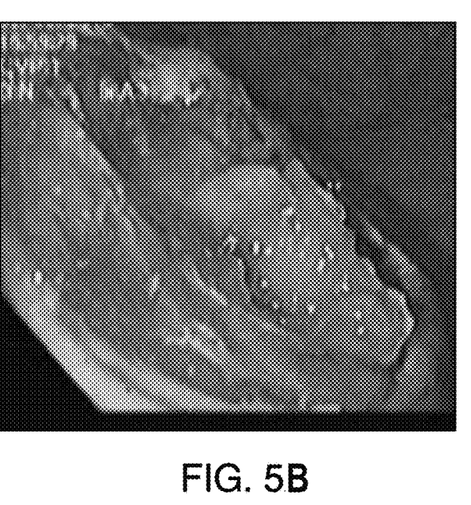
FIG. 5B illustrates an embodiment of the lesion with a protective layer of crosslinked gel where the tissue was resected using a crosslinked gel as the lifting solution.
Figure 6A:
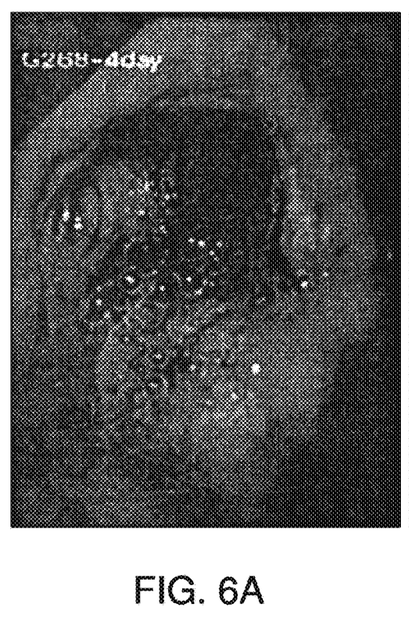
FIG. 6A illustrates a lesion 4 days after the mucosa and submucosa have been resected. The exposed tissue is irritated and bleeding.
Figure 6B:
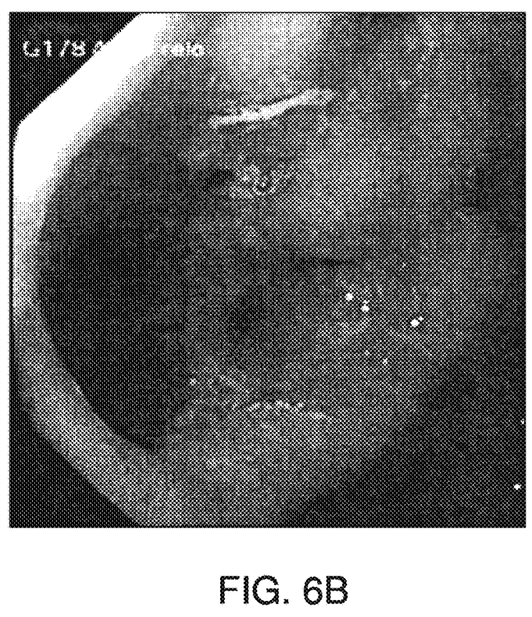
FIG. 6B illustrates an embodiment of a lesion with a protective layer of a crosslinked injectate solution 4 days after the mucosa and submucosa have been resected. As shown, the crossed linked injectate solution is still present on the lesion and the lesion is well healed.
Figure 7:
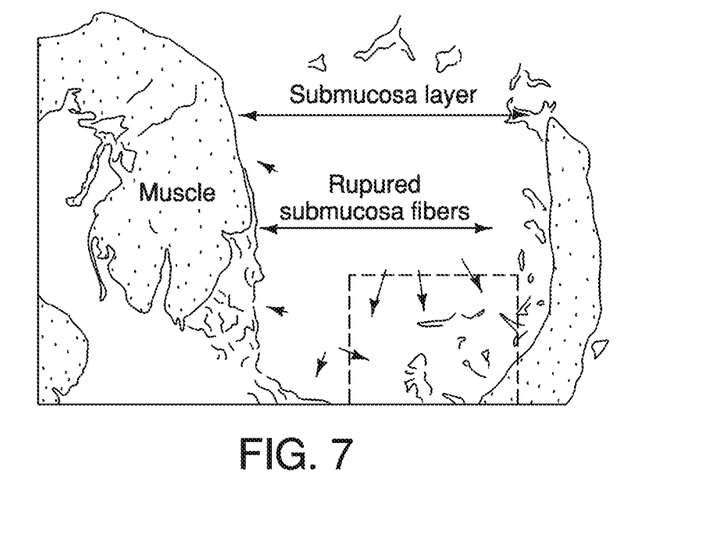
FIG. 7 shows a histological slide where the ruptured submucosal fibers can be seen in the center of the tissue.
Figure 8A:
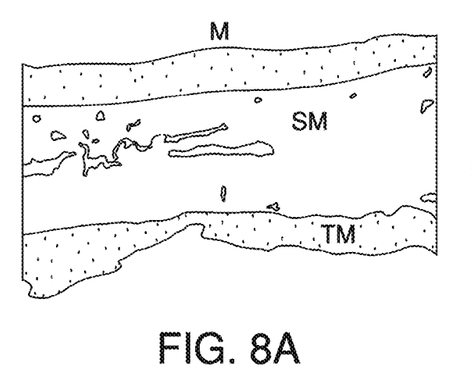
FIGS. 8A and 8B illustrate histological slides showing that uncrosslinked gel solution of 10% sodium alginate (FIG. 8A) and saline solution (FIG. 8B) did not rupture submucosal fibers.
Figure 8B:
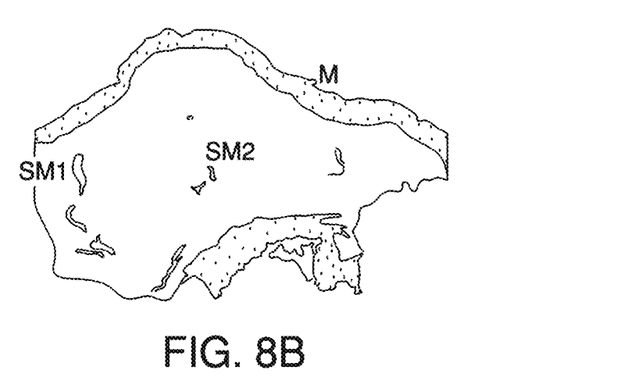

FIGS. 4-8 show tissues post injection with different injectate solutions. FIG. 4 shows raised mucosal and submucosal tissue that occurs after the injectate solution has been injected into the submucosa. The injectate solution includes 5% SrCl2 and 10% sodium alginate. FIG. 5A shows an example of the lesion after the mucosa and submucosa have been resected. This tissue was resected using convention tissue resection techniques with saline lifting solution. FIG. 5B shows an example of the lesion after the mucosa and submucosa have been resected with a protective layer of crosslinked injectate solution. This tissue was resected using a crosslinked injectate solution as the lifting solution. The crosslinked injectate solution includes 5% SrCl2 and 10% sodium alginate. FIG. 6A shows an example of a lesion 4 days after the mucosa and submucosa have been resected. As can be seen, the exposed tissue has become irritated and is bleeding. FIG. 6B shows an example of a lesion with a protective layer of a crosslinked injectate solution 4 days after the mucosa and submucosa have been resected. As shown, the crossed linked injectate solution is still present on the lesion and the lesion is well healed. The crosslinked injectate solution includes 5% SrCl2 and 10% sodium alginate. FIG. 7 shows a histological slide where the ruptured submucosal fibers can be seen in the center of the tissue. The crosslinked injectate solution includes 5% SrCl2 and 10% sodium alginate. FIGS. 8A and 8B illustrate histological slides showing that uncrosslinked gel solution of 10% sodium alginate (FIG. 8A) and saline solution (FIG. 8B) did not rupture submucosal fibers.

Figure 9:
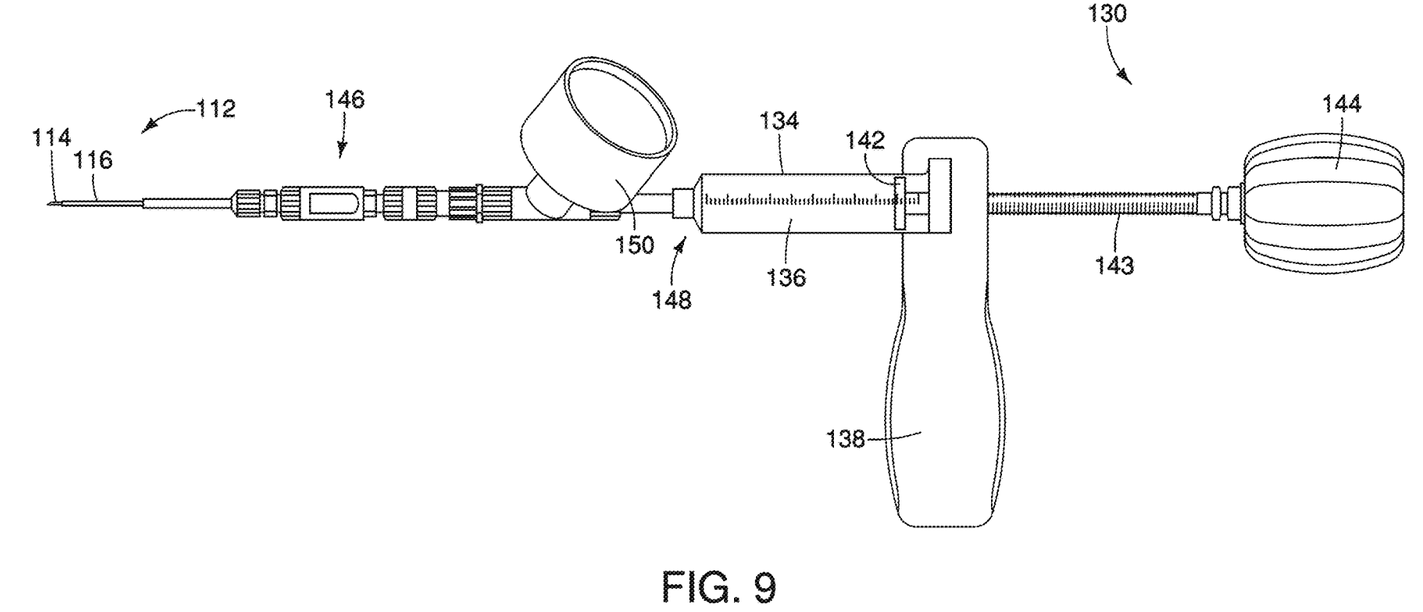
FIG. 9 shows a side view of an embodiment of a delivery device.

The injectate solution may be delivered using the delivery system 100, the distal portion 112 of an embodiment is shown in FIG. 2. An example delivery system 100 is shown in FIG. 9. Suitable delivery systems are also described in U.S. Publication No. 2011/0208158, which is incorporated by reference herein in its entirety. A proximal portion 130 of the delivery device 100 is shown in FIG. 9. The proximal portion 130 includes a housing 134 having a chamber 136 formed therein. The chamber 136 may be a dual chamber. In some embodiments the crosslinkable gel may be provided in one chamber and the crosslinker may be provided in one chamber. The device 100 further includes one or more injector handles 138 connected to the housing 134, one or more plungers 142 positioned within the housing 134, one or more plunger advancer members 143 and one or more plunger handles 144 operably connected to the plunger advancer member 143. The plunger advancer member 143 may be connected to the plunger 142 when the solution is ready to be delivered to the treatment site. In some embodiments, each chamber may have its own plunger and optionally its own plunger advance member and handle. In some embodiments, the crosslinker may be delivered separately. A connector 146 is connected to a distal end portion 148 of the housing 134. The connector 146 removably connects the inner shaft 114 and the outer catheter 116 to the distal end portion 148 of the housing 134. The inner shaft 114 may be a dual lumen shaft. In some embodiments, the dual lumens may connect at the distal tip for mixing the gel with the crosslinker. In some embodiments, the gel and the crosslinker are combined in situ. In some embodiments, a pressure gauge 150 may be included.

It is therefore intended that the foregoing detailed description be regarded as illustrative rather than limiting, and that it be understood that it is the following claims, including all equivalents, that are intended to define the spirit and scope of this invention.

The invention claimed is:

1. A method of treating a lesion site in a gastrointestinal tract; the method comprising:
    injecting a crosslinkable gel into a first tissue layer into and/or between fibers of the first tissue layer comprising delivering the gel at a pressure between about 0.25 psi and 5 psi, the crosslinkable gel increasing a volume of the first tissue layer;
    providing an electrostatic crosslinker; and
    resecting a portion of the first tissue layer having the increased volume away from a second tissue layer creating an exposed region in a remaining portion of the first tissue layer and leaving a portion of the gel covering at least a portion of the exposed region of the first tissue layer;
    crosslinking the portion of the gel to form a crosslinked gel by adding the electrostatic crosslinker to the crosslinkable gel that is in and/or between fibers of the first tissue layer, in a manner providing a protective crosslinked gel coating of said portion of the exposed region of the first tissue layer,
    wherein the electrostatic crosslinker is selected from the group consisting of magnesium chloride ($MgCl_2$), strontium chloride ($SrCl_2$), barium chloride ($BaCl_2$), barium sulfate ($BaSO_4$), calcium carbonate ($CaCo_3$), ferric chloride ($FeCl_3$) and ferrous chloride ($FeCl_2$).

2. The method according to claim 1, wherein the step of crosslinking the portion of the gel to form a crosslinked gel is performed after resecting the portion of the first tissue layer away from the second tissue layer.

3. The method according to claim 1, wherein the step of crosslinking the gel to form a crosslinked gel is performed before resecting the portion of the first tissue layer away from the second tissue layer.

4. The method according to claim 2, comprising forming the crosslinked gel having a compressive modulus of 10 to 500 kPa.

5. The method according to claim 1, wherein the crosslinker is a divalent or trivalent crosslinker.

6. The method according to claim 1, wherein the crosslinker is light activated, temperature activated, or pH activated.

7. The method according to claim 1, comprising crosslinking the gel in about 0.5 seconds to 30 minutes.

8. The method according to claim 1, comprising injecting the crosslinkable gel and the crosslinker in a single injection.

9. The method according to claim 1, wherein the first layer comprises a submucosal layer and the second layer comprises a muscularis layer, the method comprising removing a mucosal layer with the portion of the submucosal layer from the muscularis layer.

10. The method according to claim 1, wherein the first layer comprises oral lymphoid tissue and the second layer comprises a muscularis layer.

11. The method according to claim 2, wherein the crosslinked gel is capable of remaining at the portion of the exposed region of the first tissue layer for a minimum of about 24 hours.

12. The method according to claim 1, comprising injecting the crosslinkable gel having a maximum viscosity of 100,000 cP.

13. The method according to claim 1, wherein the crosslinker is provided before the crosslinkable gel is injected.

14. An injectate system comprising:
a crosslinkable gel; and
an electrostatic crosslinker for crosslinking the gel, the crosslinkable gel and the crosslinker forming a crosslinked gel having a compressive modulus of about 10-500 kPa,
wherein the injectate system is configured to deliver a gel at a pressure between about 0.25 psi and 5 psi into a portion of a gastrointestinal tract.

15. The system according to claim 14, wherein the crosslinkable gel is selected from the group consisting of agarose, alginate, carbomer, carboxymethyl cellulose, collagen, fibronectin, chitosan, chondroitin sulfate, dextran, polyethylene glycol, polyvinylpyrolidone, silicone, poly (hydroxyethyl methacrylate), polyacrylic acid, polyacrylamide, polyvinyl alcohol, gelatin, mucin, heparin, and hyaluronan.

16. The system according to claim 14, wherein the crosslinker is a divalent crosslinker or a trivalent crosslinker.

17. The system according to claim 16, wherein the crosslinker is selected from the group consisting of magnesium chloride ($MgCl_2$), strontium chloride ($SrCl_2$), barium chloride ($BaCl_2$), barium sulfate ($BaSO_4$), calcium carbonate ($CaCo_3$), ferric chloride ($FeCl_3$) and ferrous chloride ($FeCl_2$).

* * * * *